(12) United States Patent
Omura et al.

(10) Patent No.: US 6,790,968 B1
(45) Date of Patent: Sep. 14, 2004

(54) SUBSTANCE FKI-0076 AND PROCESS FOR PRODUCING THE SAME

(75) Inventors: Satoshi Omura, Tokyo (JP); Hiroshi Tomoda, Tokyo (JP); Rokuro Masuma, Tokyo (JP); Masayoshi Arai, Tokyo (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 10/169,551

(22) PCT Filed: Mar. 6, 2000

(86) PCT No.: PCT/JP00/01348

§ 371 (c)(1),
(2), (4) Date: Oct. 24, 2002

(87) PCT Pub. No.: WO01/66537

PCT Pub. Date: Sep. 13, 2001

(51) Int. Cl.[7] .................. C07D 309/36; C12P 17/06; C12N 1/14
(52) U.S. Cl. .................. 549/416; 435/118; 435/125; 435/254.1
(58) Field of Search .................. 435/254.1, 118, 435/125; 549/416

(56) References Cited

FOREIGN PATENT DOCUMENTS

JP          58-209986          12/1983

OTHER PUBLICATIONS

E. J. Anaissie et al., "Management of Invasive Candidal Infections: Results of a Prospective, Randomized, Multicenter Study of Fluconazole Versus Amphotericin B and Review of the Literature", Clinical Infectious Disease, 1996, vol. 23, pp 964–72.
H. V. Bossche et al., "Characterization of an Azole–Resistant Candida Glabrata Isolate", Antimicrobial Agents and Chemotheapy, Dec. 1992, vol. 36, No. 12, pp 2602–2610.
D. Sanglard et al., "Amino Acid Substitutions in the Cytochrome P–450 Lanosterol 14a– Demethylase (CYP51A1) from Azole–Resistant *Candida albicans* Clinical Isolates Contribute to Resistance to Azole Antifungal Agents", Antimicrobial Agents and Chemotherapy, Feb. 1998, vol. 42, No. 2, pp 241–253.

M. E. Fling et al., "Analysis of a *Candida albicans* gene that encodes a novel mechanism for resistance to benomyl and methotrexate", Mol Gen Genet, 1991, pp 318–329.

D. Sanglard et al., "Cloning of *Candida albicans* genes conferring resistance to azole antifungal agents: characterization of CDR2, a new multidrug ABC transporter gene", Microbiology, 1997, pp 405–416.

H. B. V. D. Hazel et al., "PDR16 and PDR17, Two–Homologous Genes of *Saccharomyces cerevisiae*, Affect Lipid Biosynthesis and Resistance to Multiple Drugs", The Journal of Biological Chemistry, vo. 274, No. 4, pp 1934–1941.

M. Takeuchi et al., "Fosfonochlorin, A New Antibiotic With Spheroplast Forming Activity", The Journal of Antibiotics, Feb. 1989, pp 198–205.

*Primary Examiner*—Herbert J. Lilling
(74) *Attorney, Agent, or Firm*—Young & Thompson

(57) ABSTRACT

A microorganism having ability to produce FKI-0076 substance represented by the following formula [I]

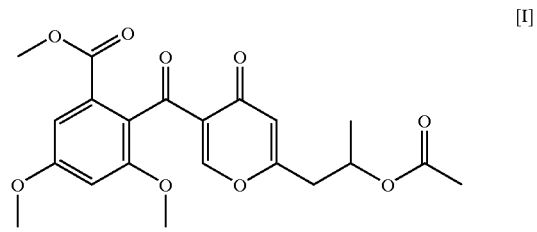

is cultured in a medium allowing for the accumulation of FKI-0076 substance in the culture liquid. The FKI-0076 substance from can then be isolated the cultured mass. Since the substance has the ability to enhance azole antifungal agents, it provides an action against various fungal infections such as deep-seated mycosis and other fungal infections in low concentration and within a short term. Consequently, the FKI-0076 is useful for reducing the frequency of appearance of resistant microorganisms. Further, usefulness for overcoming resistance is expected.

5 Claims, 4 Drawing Sheets

SUBSTANCE FKI-0076 AND PROCESS FOR PRODUCING THE SAME

BACKGROUND OF THE INVENTION

1. Field of the Invention

The present invention relates to novel FKI-0076 substance having potentiation activity for azole antifungal agents and production thereof.

2. Description of Related Art

Azoles specifically used for treatment of diseases such as deep-seated mycosis, for example, miconazole {1-[2,4-dichlorobenzyloxy]-2-(2-,4-dichlorophenyl)ethyl} imidazole: Sigma Inc.}, fluconazole [2,4-difluoro- α, α-bis(1H,1,2,4-triazol-1-yl-methyl) benzyl alcohol: ICN Pharmaceuticals Inc.] and itraconazole ((±)-1-Sec-butyl-4-[P-[4-[P-[[2R,4S]-2-(2,4-dichlorophenyl)-2-(1H-1,2,4-triazol-1-yl-methyl)-1,3-dioxolan-4-yl]methoxy]phenyl]-piperazinyl]phenyl}-$\Delta^2$-1,2-,4-triazolin-5-one: Kyowa Hakko Kogyo K. K.), are highly safe as compared with the most frequently used polyenes, amphotericin B, for treatment of such diseases (Anaissie E. J. et al., Clinical Infectious Diseases, 23: 964–972, 1996). However, recently, the appearance of resistant strains of microbes caused by long-term or repetitive administration of these azole antimicrobial agents has become a problem. As a result, the development of drugs with a high level of safety and a low level of resistance exhibited by microorganisms is urgently necessary.

SUMMARY OF THE INVENTION

In diseases accompanied with immunocompromised conditions such as HIV infection and hematologic disease, the compromised host condition is induced, and the risk of developing a fungal infection is increased as an opportunistic infection. Diseases with these immunocompromised conditions are frequently serious, and long-term therapy is required. Consequently, at present the most frequently used azole antifungal agents may not be used to present inducing drug resistance, since the long term chemotherapy of fungal infection is required in many cases.

A mechanism of resistance against azole antifungal agents is known as follows. In *Candida albicans*, the target enzyme, P-450, i.e. excess expression of 14-α-demethylase or decrease in affinity with drug as a result of amino acid mutation (Vanden Bossche, H. et al. Antimicrobial Agents and Chemotherapy, 36, 2602–2610, 1992; Sanglard, D. et al., ibid., 42, 241–153, 1998) and decrease in intracellular drug concentration by the multiple drug excretion transporter (Fing, M. E. et al., Mol. Gen. Gent., 227, 318–329, 1991; Sanglard, D. et al., Microbiology, 143, 405–416, 1997) are known. In *Saccharomyces cerevisiae*, it has reported that MDR (Multiple Drug Resistant) genes, PDR16 and PDR17, could change the lipid metabolism to acquire the resistance against azole compounds (H. Bart van den Hazel, et al., J. Biol. Chem., 274, 1934–1941, 1999).

Consequently, the drugs, which can increase activity of azole antifungal agents, may be expected to decrease the frequency of appearance of the resistant microorganisms by reducing the amount of the administration of the drug as well as shortening the administration term. Further, as a result of use in combination with drugs having two different skeletal structures, the resistance against azole antifungal agents can be overcome.

In such condition, to provide drugs having enhanced activity of azole antifungal agents is useful for the treatment of various fungal infections such as deep-seated mycosis.

We have found that, as a result of studies on metabolites produced by various microorganisms, a substance having properties to activate azole antifungal agents was produced in a cultured mass of the strain FKI-0076 which was newly isolated from soil. We have also found, as a result of isolating and purifying the active substance from the cultures mass, the substance having the chemical structure shown in the formula [I] hereinafter and designated as FKI-0076 substance due to its unknown chemical structure.

The present invention was obtained as a result of these findings. The present invention relates to FKI-0076 substance indicated by the chemical structure [I] hereinbelow.

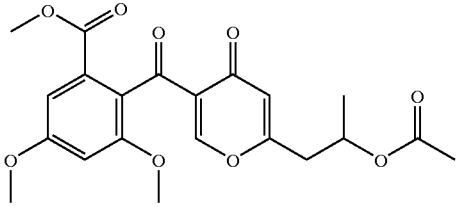

The present invention also relates to the FKI-0076 substance having the following physicochemical properties.

(1) Nature: yellow oily substance.
(2) Molecular weight: 418 (fast atom bombardment mass spectrometry)
(3) Molecular formula: $C_{21}H_{22}O_9$.
(4) Optical rotation: $[\alpha]_D^{25}=+5.2°$ (c=0.23, methanol)
(5) DV spectrum: Ultraviolet absorption spectrum measured in methanol as shown in FIG. 1, and has a specific absorption maximum at 208 nm ($\epsilon$=34900), 246 nm ($\epsilon$=11000) and 314 nm ($\epsilon$=3950).
(6) IR spectrum: Infrared absorption spectrum measured in KBr tablet as shown in FIG. 2 and has specific absorption bands at 3410, 1735, 1724, 1683, 1658, 1602 and 1579 $cm^{-1}$.
(7) $^1$H-NMR spectrum: As shown in FIG. 3 (measured by using NRM spectrometer, Varian Japan, in $CDCl_3$).
(8) $^{13}$C-NMR spectrum: As shown in FIG. 4 (measured by using NRM spectrometer, Varian Japan, in $CDCl_3$).
(9) Solubility in solvents: Soluble in methanol, chloroform and ethyl acetate.
Slightly soluble in hexane.
(10) Color reaction: Positive in molybdic acid
(11) Differentiation in acidic, neutral and alkaline nature: Neutral substance.

The present invention further relates to a process for production of FKI-0076 substance comprising culturing a microorganism belonging to *Talaromyces flavus* capable of producing FKI-0076 substance, accumulating FKI-0076 substance in the cultured mass and isolating FKI-0076 substance from the cultured mass.

The present invention further relates to the process for producing FKI-0076 substance wherein the microorganism is capable of producing FKI-0076 substance is *Talaromyces flavus* FKI-0076 FERM BP-7037. The present invention further relates to the microorganism capable of producing FKI-0076 substance wherein the microorganism is *Talaromyces flavus* FKI-0076 FERM BP-7037.

A preferable example of the microorganism strain of the present invention used for production of FKI-0076 substance is the strain of *Talaromyces flavus* FKI-0076, which was newly isolated from soil by the inventors of the present invention.

Taxonomical properties of the microorganism strain are shown as follows.

1. Morphological Properties:

Good growth is observed in Czapek-yeast extract agar medium, oatmeal agar medium, malt extract agar medium and cornmeal agar medium and large numbers of ascocarps covered with yellow to orange colored soft hyphae are observed. Many penicili are observed on cornmeal agar. On the other hand, on 25% glycerol nitrate agar medium, growth is suppresed without observing ascocarps and only penicili are observed. On day 7, growth is more rapid at 37° C. in the Czapek-yeast extract agar medium than at 25° C., but no matured ascocarps are observed.

Ascocarps are spherical with diameter of 300–800 $\mu$m and are matured within 10 days. Ascocarp primordium is grown with the ascogone coiling around the club-shaped antheridium. The shape of the ascus is spherical to aspherical (8.8–11.0×7.5–10.0 $\mu$m) and disappears with maturation. The ascospore is ellipsoidal (3.5–4.5×2.5–3.5 $\mu$m) with spiny spikes covering the whole surface.

The conidiophore of penicili grow from substrate mycelium and aerial mycelium with longer conidiophore of the length of 180–250 $\mu$m grown from substrate mycelium, on the other hand, the length of the conidiophore is shorter with a length of 50–120 $\mu$m. The penicili forms monoverticillate to biverticillate. Metula is 12.5–17.5×2.5–3.0 $\mu$m with growing 2–4metulae in colonies. A pen point shaped phialide has a length of 11.0–15.0×1.8–3.0 $\mu$m with 3–6 verticillates in the metulae. The conida were elliptical with a length of 2.0–3.0×1.5–2.5 $\mu$m and the surface is smooth.

2. Cultured Properties on Various Agar Medium

Results of macroscopic observation cultured on various agar media at 25° C. for 14 days are shown in Table 1.

TABLE 1

| Medium (diameter of colony) Growth on medium | Color of surface of colony | Color of reverse side of colony |
|---|---|---|
| Czapek-Yeast extract (62–64 mm) floccose - velvety corrugate, entire | yellow - orange yellow | yellow - ocher |
| Oat meal agar medium (75–77 mm) floccose, entire | yellow - orange | yellow |
| Malt extract agar medium (30–32 mm) floccose - velvety slightly irregular, filamentous | lemon | yellow |
| Cornmeal agar medium (65–67 mm) floccose, entire | white - yellow | white - pale yellow |
| 25% glycerol nitrate agar medium (4–10 mm) powdery, irregular | gray green | dark gray |

3. Physiological Properties

1) Optimum growth condition

Optimum growth condition of the strain is pH 4–7 at 19.5–31.5° C.

2) Growth range of the strain is pH 3–7 at 9.0–37.5° C.

3) Differentiation of aerobic or anaerobic: aerobic.

As described hereinabove, as a result of comparative studies based on the morphological properties, culture properties and physiological properties of the strain FKI-0076 with known strains, this strain was identified as a strain belonging to *Talaromyces flavus* and referred as *Talaromyces flavus* FKI-0076. This strain was deposited with the name of *Talaromyces flavus* FKI-0076 in the International Patent Organism Depository, National Institute of Advanced Industrial Science and Technology, Higashi 1-1-3, Tsukuba-city, Ibaragi-ken, Japan and given a permanent depository No. as FERM BP-7037 on Feb. 21, 2000.

An example of the FKI-0076 substance producing strain used in the present invention is the aforesaid *Talaromyces flavus* FKI-0076. As a general nature of the microorganism, the strain is easily mutated and not constantly maintained in its nature. It is well known to mutate the microorganism naturally or artificially by using ultraviolet irradiation, X-ray irradiation or treating the microorganism with mutagenic agents such as N-methyl-N'-nitro-N-nitrosoguanidine or 2-aminopurine. The strains belonging to *Talaromyces flavus* including artificial mutants, cell fusion strain and genetically engineered strain and producing FKI-0076 substance can be used in the present invention.

In the production of FKI-0076 substance of the present invention, the FKI0076 producing strain belonging to *Talaromyces flavus* is cultured in a preferable medium. Examples of preferable nutrient sources are assimilable carbon sources, digestible nitrogen sources, and if necessary inorganic salts, vitamin, etc.

The above described assimilable carbon sources are saccharides such as glucose, fructose, maltose, lactose, galactose, dextrin, starch, and plant oil such as soybean oil, used alone or in combination with each other.

Examples of digestible nitrogen sources are peptone, yeast extract, meat extract, soybean powder, cotton seed powder, corn steep liquor, malt extract, casein, amino acids, urea, ammonium salt or nitrate and are used alone or in combination with each other. If necessary, salts such as phosphate, magnesium salt, calcium salt, sodium salt or potassium salt, and heavy metallic salt such as iron salt, manganese salt, copper salt, cobalt salt and zinc salt, various vitamins and substance preferable for production of FKI-0076 substance are preferably added.

In the culture, if necessary, antifoam agent such as liquid paraffin, animal oil, plant oil and silicone oil can be added in case of foaming. The above culture can be a liquid culture or solid culture, if the above nutrient sources are contained. Conventionally, it is preferable to use a liquid culture. In case of small scale culture, a culture using a flask is preferable. In large scale industrial production, a submerged aeration culture as like in the other fermentation production is preferable.

In case of a large scale culture in a large tank, in order to prevent a growth delay of the microorganisms in the production process, at first, the strain for production is inoculated into a comparatively small scale medium, subsequently, the cultured mass is transferred into the large tank and cultured for mass production. In this case, the composition of medium of the former culture and the composition of the medium used in the production scale can be identical with each other or, if necessary, can be changed.

In case an aeration culture is used with stirring, conventionally known methods can be applied. For example, agitation by propeller and other machinery means, rotation or shaking of the fermentor, pumping treatment and blowing aeration can be used. Aeration is sterilized before use.

The culturing temperature can be changed within the range of production of FKI-0076 substance by the FKI-0076 substance producing temperature and is 20–30° C., preferably around 27° C. The culturing pH is usually pH 5–8, preferably neutral pH 7. The culturing time is different depending on the culture condition and is generally around 4–7 days.

The thus obtained FKI-0076 substance exists in the cultured mycelia and culture filtrate. In order to isolate the FKI-0076 substance from the cultured mass, the whole cultured mass is extracted with water miscible organic solvent such as acetone, and the solvent is distilled off in vacuo, subsequently the residue is extracted with a water immiscible organic solvent such as ethyl acetate.

In addition to the above extraction method, known methods used for the isolation of a lipophilic substance, for example, absorption chromatography, gel filtration chromatography, thin-layer chromatography, centrifugal counter-current chromatography and high performance liquid chromatography are preferably combined or repeatedly performed to isolate each component and purified.

The physicochemical properties of FKI-0076 of the present invention are as follows.
(1) Nature: yellow oily substance.
(2) Molecular weight: 418 (fast atom bombardment mass spectrometry)
(3) Molecular formula: $C_{21}H_{22}O_9$.
(4) Optical rotation: $[\alpha]_D^{25}=+5.20°$ (c=0.23, methanol)
(5) UV spectrum: Ultraviolet absorption spectrum measured in methanol as shown in FIG. 1, and has specific absorption maximum at 208 nm ($\epsilon$=34900), 246 nm ($\epsilon$=11000) and 314 nm ($\epsilon$=3950).
(6) IR spectrum: Infrared absorption spectrum measured in KBr tablet as shown in FIG. 2 and has specific absorption bands at 3410, 1735, 1724, 1683, 1658, 1602 and 1579 $cm^{-1}$.
(7) $^1$H-NMR spectrum: As shown in FIG. 3 (measured by using NRM spectrometer, Varian Japan, in $CDCl_3$).
(8) $^{13}$C-NMR spectrum: As shown in FIG. 4 (measured by using NRM spectrometer, Varian Japan, in $CDCl_3$).
(9) Solubility in solvents: Soluble in methanol, chloroform and ethyl acetate.
Slightly soluble in hexane.
(10) Color reaction: Positive in molybdic acid
(11) Differentiation in acidic, neutral and alkaline nature: Neutral substance.

As a result of careful examination of the above various physicochemical properties and spectral data of FKI-0076 substance, the present FKI-0076 substance was determined to have the following chemical structure [I].

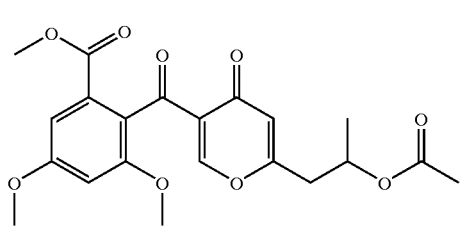

[I]

As described hereinabove, the physicochemical properties of FKI-0076 substance were described in detail. A compound having these properties has never been reported previously. Consequently, the FKI-0076 substance of the present invention is determined as a novel substance.

The biological properties of FKI-0076 substance of the present invention will be explained in detail.

(1) Enhanced Activity of Azole Antifungal Agent

Enhanced activity of azole antifungal agent is determined by the following method.

*Candida albicans* KF1 and *Saccharomyces cerevisiae* KF26 (ATCC 9763) were used. *Candida albicans* KF1 was cultured in Waksman broth (glucose 2.0%, peptone 0.5%, meat extract 0.5%, and NaCl 0.5%, pH 7.0) and *Saccharomyces cerevisiae* KF26 was cultured in potato broth (glucose 1.0%, peptone 0.5% and potato extract 100 ml). Both strains were cultured at 27° C. for 40 hours. Subsequently, each strain was inoculated in GY agar medium (glucose 1.0%, yeast extract 0.5% and agar 0.8%, pH 6.0). In addition, an amount of 0.3%. Miconazole (Sigma Chemicals, Inc.) was used as the azole antifungal agent. The amount of addition to the GY agar medium was set as 0.1 μg/ml (final concentration), a concentration which does not affect to the growth of both test microorganisms. Activities were assessed using paper disc (thickness: 8 mm, ADVANTEC Inc.). After being cultured at 27° C. for 24 hours, the diameter of the inhibitory zone was measured for each organism.

As for the results, FKI-0076 substance did not show an inhibitory ring at a concentration of 100 μg without addition of miconazole. On the other hand, when miconazole was added, the concentration of 100 μg inhibited *Saccharomyces cerevisiae* KF26 to inhibition ring of 25 mm, and *Candida albicans* KF1 was inhibited to an inhibition ring of 15 mm.

(2) Antimicrobial Action Against Various Test Microorganisms

Minimum inhibitory concentration (MIC) against various test microorganisms was assayed using the microbroth dilution method (M. Suzanne, et al. J. Biol. Chem., 272, 32709–32714, 1997).

Namely, test microorganisms were prepared at the concentration of $2 \times 10^4$–$1 \times 10^5$ cells/ml and cultured with FKI-0076 substance at the concentration of 0–125 μg. Growth of each test microorganism was determined by the measured value at OD 600 nm. The culture temperature for *Xanthomonas campestris* pv. *oryzae*, *Pyricularia oryzae*, *Aspergillus niger*, *Mucor racemosus*, *Candida albicans* and *Saccharomyces cerevisiae* was set at 27° C. and other microorganisms were set at 37° C. Culture tire was set for 48 hours for *Pyricularia oryzae* and *Aspergillus niger* and other strains were set for 24 hours. Minimum inhibitory concentration (MIC) against various microorganisms is shown in Table 2.

TABLE 2

| Test Organism | MIC (μg/ml) |
| --- | --- |
| *Bacillus subtilis* KB27 (ATCC6633) | >125 |
| *Staphylococcus aureus* KB210 (ATCC6538P) | >125 |
| *Micrococcus luteus* KB40 (ATCC9431) | >125 |
| *Mycobacterium smegmatis* KB42 (ATCC607) | >125 |
| *Escherichia coli* KB176 (IF012734) | >125 |
| *Pseudomonas aeruginosa* KB105 (IF03080) | >125 |
| *Xanthomonas campestris* pv. *oryzae* KB88 | >125 |
| *Acholeplasma laidlawii* KB174 | 125 |
| *Pyricularia oryzae* KB180 | 125 |
| *Aspergillus niger* KB103 (ATCC6275) | >125 |
| *Mucor racemosus* KF223 (IF04581) | >125 |
| *Candida albicans* KF1 | >125 |
| *Saccharomyces cerevisiae* KF26 (ATCC9763) | >125 |

As described hereinabove, the novel substance of the present invention enhanced action for azole antifungal agents and exhibits action against deep-seated mycosis and other fungal infectious diseases at a low concentration and within a short time the substance is useful for reducing the frequency resistant microorganisms. Further, usefulness for overcoming the resistance will be expected.

DETAILED DESCRIPTION OF THE PREFERRED EMBODIMENTS

Figure 1:
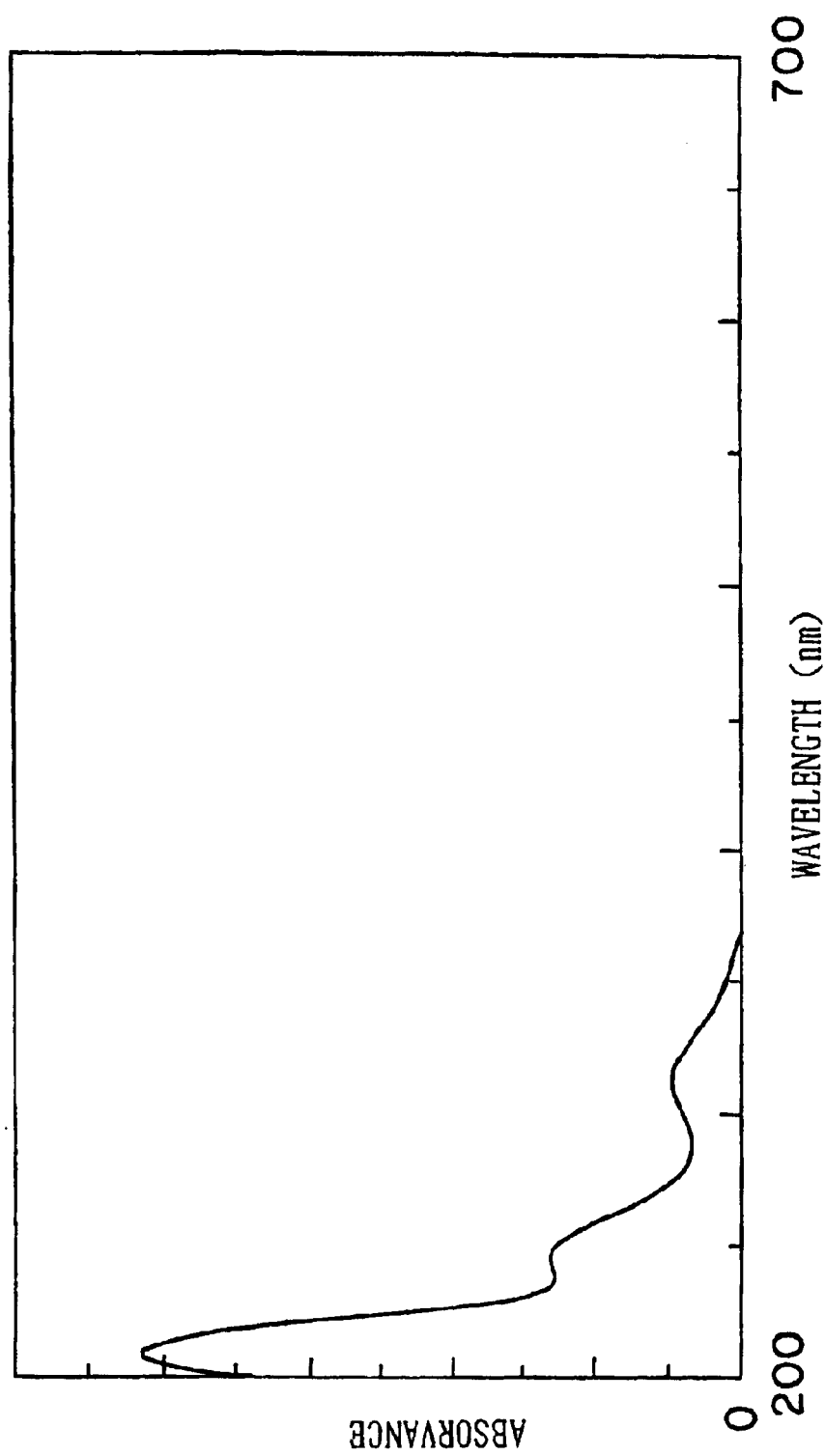
FIG. 1 shows UV absorption spectrum (in methanol) of FKI-0076 substance of the present invention.

While the present invention will be explained concretely by mentioning examples, but the present invention is not limited within these examples.

EXAMPLE

A mixture (100 ml) of glucose 2.0%, yeast extract 0.2%, polypeptone 0.5%, MgSO$_4$·7H$_2$O 0.05%, potassium dihydrogenphosphate 0.1% and agar 0.1% (adjusted to pH 6.0) was added to two 500 ml Erlenmeyer flasks, respectively. Flasks were sealed with a cotton plug and, sterilized with steam. One loopful of *Talaromyces flavus* FKI-0076 grown on the agar medium was aseptically inoculated and shake cultured at 27° C. for 72 hours to prepare a seed culture medium.

The medium containing potato dextrose broth 2.4%, maltose extract 0.5%, Mg$_3$(PO$_4$)$_2$·8H$_2$O 0.5% and agar 0.1% (adjusted at pH 6.0) in a 30 L jar fermentor (Mitsuwa Inc.) was sterilized with steam. The seed cultured medium was inoculated aseptically and cultured at 27° C. for 5 days. Acetone was added to the obtained whole cultured liquid, stirred well, and concentrated in vacuo. This was again extracted with ethyl acetate and concentrated in vacuo to obtain crude substance 12 g.

The crude substance 2.5 g was charged on a column of the middle pressure liquid chromatography (ODS resin, Senshu Sci. Co.) and eluted with acetonitrile and water. The apparatus used was LIQUID chromatograph 6300 (Senshu Sci. Inc.) with a flow rate of 10 ml/min. The solvent used for elution was started with 80% acetonitrile-water and after 180 minutes, the eluate was scheduled to be 30% acetonitrile-water in the linear gradient elution. Each fraction was fractionated in 15 ml fractions. The active fractions containing active component from fraction No. 85 to No. 100 were collected, removed the acetonitrile, and the aqueous layer was extracted with ethyl acetate and dried up in vacuo to obtain crude product 1.36 g.

The crude product 1.36 g was isolated and purified by using high performance liquid chromatography. The apparatus used was PU-980 (Nihon Bunko Inc.) with a column YMC-Pack ODS-AM column (ODS resin, 20×250 mm, Yamamura Chem. Inst.). The solvent system was 45% aqueous acetonitrile and the detection was performed with UV 230 nm, flow rate 6 ml/min. As a result, 10 mg of FKI-0076 substance was isolated.

EFFECT OF THE INVENTION

As explained hereinabove, since the novel FKI-0076 substance has enhanced activity for azole antifungal agents, it provides an action against deep-seated mycosis and other fungal infections at a low concentration and within a short term, FKI-0076 substance is effective for reducing the frequency of appearance of resistant microorganisms. Further, usefulness for overcoming resistance will be expected.

What is claimed is:

1. FKI-0076 substance represented by the following formula [1]:

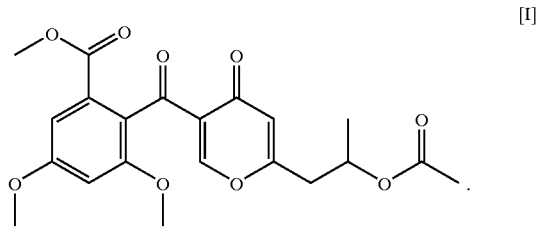

Figure 2:
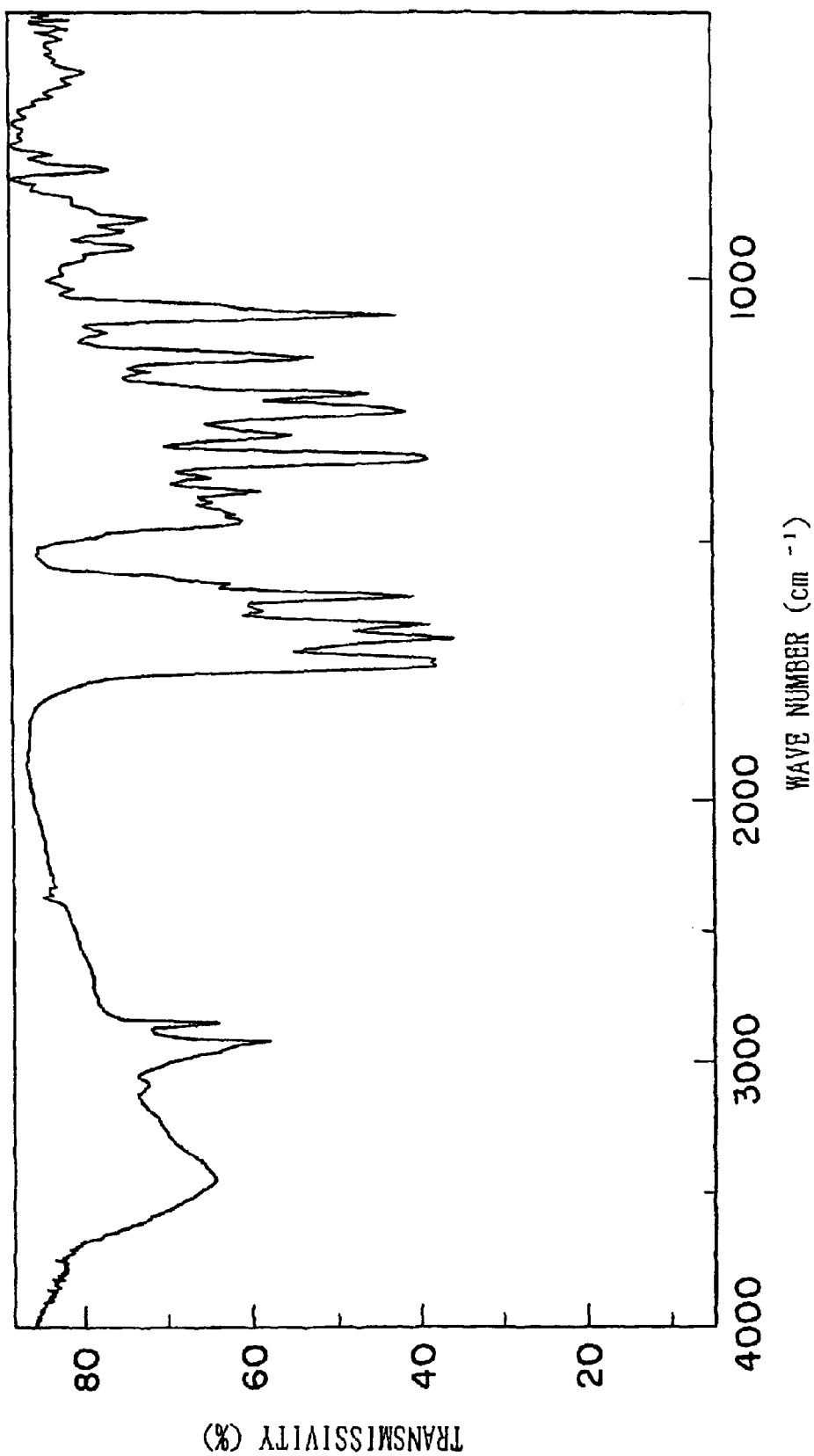
FIG. 2 shows IR absorption spectrum (KBr tablet) of FKI-0076 substance of the present invention.
Figure 3:
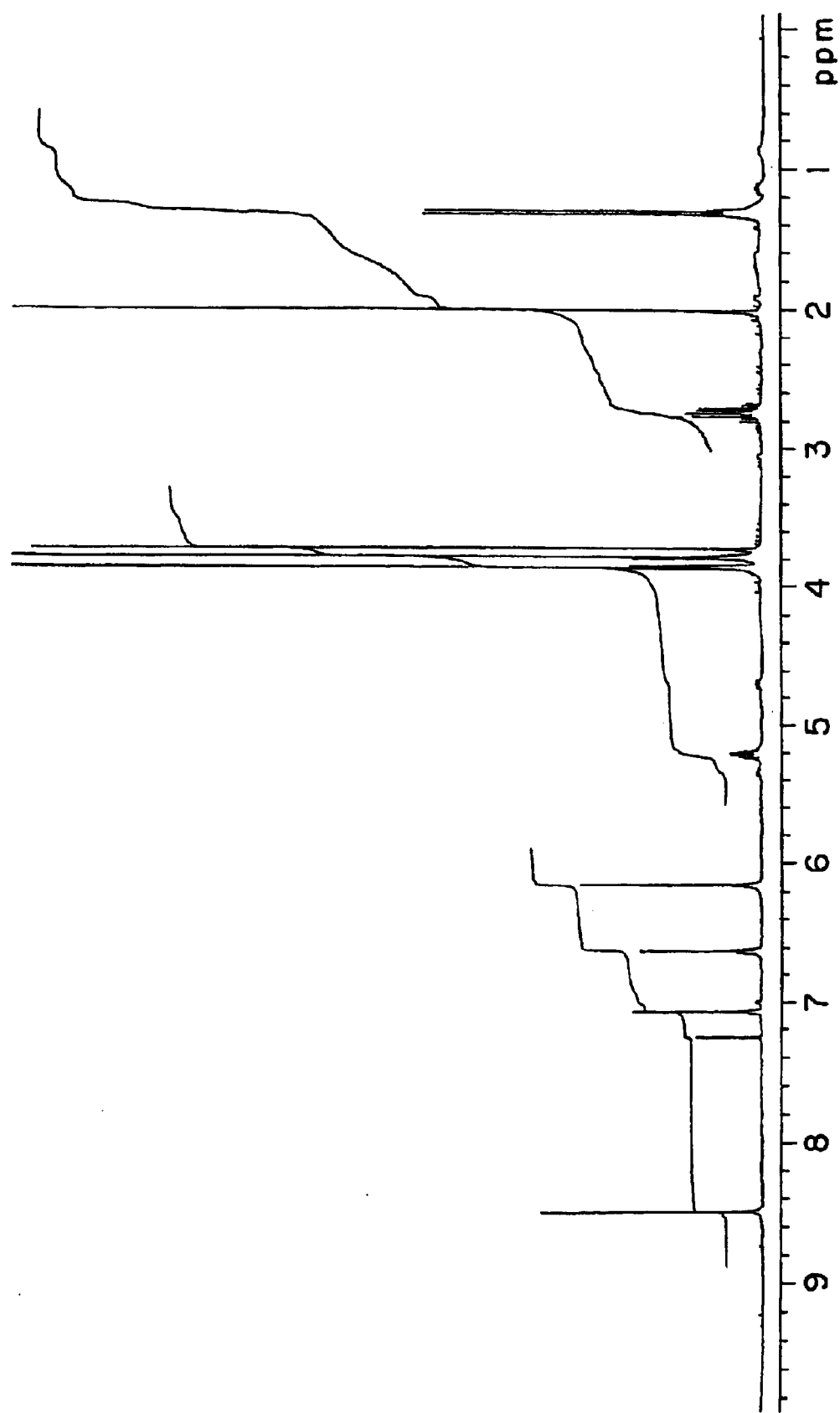
FIG. 3 shows proton NMR spectrum of FKI-0076 substance of the present invention (in CDCl$_3$).
Figure 4:
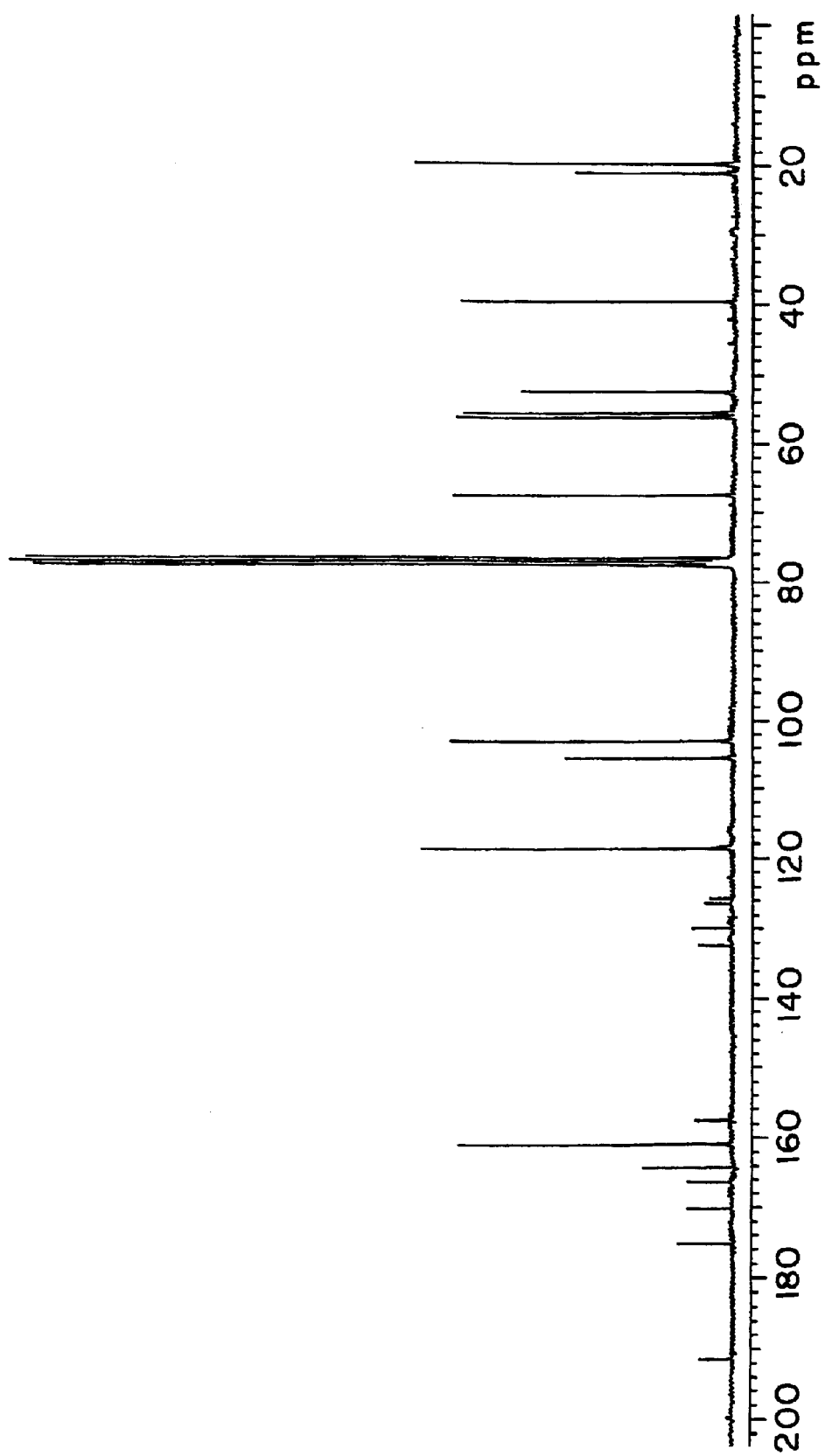
FIG. 4 shows $^{13}$C NMR spectrum of FKI-0076 substance of the present invention (in CDCl$_3$).

2. FKI-0076 substance having following physicochemical properties:
   (1) Nature: yellow oily substance.
   (2) Molecular weight: 418 (fast atom bombardment mass spectrometry)
   (3) Molecular formula: C$_{21}$H$_{22}$O$_9$.
   (4) Optical rotation: $[\alpha]_D^{25}$=+5.2° (c=0.23, methanol)
   (5) UV spectrum: Ultraviolet absorption spectrum measured in methanol as shown in FIG. 1, and has specific absorption maximum at 208 nm ($\epsilon$=34900), 246 nm ($\epsilon$=11000) and 314 nm ($\epsilon$=3950).
   (6) IR spectrum: Infrared absorption spectrum measured in KBr tablet as shown in FIG. 2 and has specific absorption bands at 3410, 1735, 1724, 1683, 1658, 1602 and 1579 cm$^{-1}$.
   (7) $^1$H-NMR spectrum: As shown in FIG. 3 (measured in CDCl$_3$).
   (8) $^{13}$C-NMR spectrum: As shown in FIG. 4 (measured in CDCl$_3$).
   (9) Solubility in solvents: Soluble in methanol, chloroform and ethyl acetate.
   Slightly soluble in hexane.
   (10) Color reaction: Positive in molybdic acid
   (11) Differentiation in acidic, neutral and alkaline nature: Neutral substance.

3. A process for producing of FKI-0076 substance, comprising: culturing a microorganism belonging to *Talaromyces flavus* said microorganism having an ability to produce FKI-0076 substance in a culture medium, accumulating said FKI-0076 substance in the culture liquid medium and isolating said FKI-0076 substance from said culture medium.

4. The process according to claim 3, wherein said microorganism belonging to *Talaromyces flavus* and having ability to produce FKI-0076 substance is *Talaromyces flavus* FKI-0076 FERM BP-7037.

5. A microorganism *Talaromyces flavus* FKI-0076 FERM BP-0076 wherein said microorganism belongs to *Talaromyces flavus* and has the ability to produce FKI-0076 substance.

* * * * *